US007313439B2

(12) United States Patent
Jackson et al.

(10) Patent No.: US 7,313,439 B2
(45) Date of Patent: Dec. 25, 2007

(54) METHOD AND APPARATUS FOR PREDICTING ARRHYTHMIAS USING DIURNAL HEART RATE

(75) Inventors: Troy E Jackson, New Brighton, MN (US); Paul A Belk, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 214 days.

(21) Appl. No.: 11/004,176

(22) Filed: Dec. 3, 2004

(65) Prior Publication Data

US 2005/0137489 A1 Jun. 23, 2005

Related U.S. Application Data

(60) Provisional application No. 60/526,563, filed on Dec. 3, 2003.

(51) Int. Cl.
  *A61N 1/365* (2006.01)
(52) U.S. Cl. .......................... 607/19; 600/519; 607/25
(58) Field of Classification Search ................ 600/515, 600/518–520, 509, 513; 607/14, 17–19, 607/9, 25
See application file for complete search history.

(56) References Cited

U.S. PATENT DOCUMENTS

| 4,428,378 A | 1/1984 | Anderson et al. ...... 128/419 PG |
| 5,042,497 A | 8/1991 | Shapland ................... 128/696 |
| 5,117,824 A | 6/1992 | Keimel et al. .......... 128/419 D |
| 5,545,186 A | 8/1996 | Olson et al. ................. 607/14 |
| 5,718,235 A | 2/1998 | Golosarsky et al. ........ 128/708 |
| 5,861,011 A * | 1/1999 | Stoop ........................... 607/25 |
| 5,891,044 A | 4/1999 | Golosarsky et al. ........ 600/509 |
| 5,967,995 A | 10/1999 | Shusterman et al. ........ 600/516 |
| 6,067,473 A | 5/2000 | Greeninger et al. .......... 607/32 |
| 6,171,252 B1 | 1/2001 | Roberts ....................... 600/485 |

(Continued)

FOREIGN PATENT DOCUMENTS

EP      0 472 411 A1    2/1992

(Continued)

OTHER PUBLICATIONS

Bansch, D. et al., "Clusters of Ventricular Tachycardias Signify Impaired Survival in Patients with Idiopathic Dilated Cardiomyopathy and Implantable Cardioverter Defibrillators," *J Am Coll Cardiol*, vol. 36, No. 2, p. 566-73 (Aug. 2000).

(Continued)

*Primary Examiner*—Kennedy J. Schaetzie
*Assistant Examiner*—Jessica L. Reidel
(74) *Attorney, Agent, or Firm*—Michael C. Soldner

(57) ABSTRACT

A method of predicting an arrhythmia, such as ventricular tachycardia, for example, in a medical device using a quantitative measure in order to allow assessment of patient risk and to enable preventative interventions by the device and clinicians. The trending of day and night average heart rates, along with patient physical activity can be analyzed to provide prediction of impending arrhythmia within weeks. By examining day and night average heart rate for crossover points, where the night heart rate equals or exceeds the day rate, and monitoring for a concomitant elevation in the night heart rate from a reference value, specific days heralding an increased risk of arrhythmia can be determined and therapy can be updated accordingly.

4 Claims, 3 Drawing Sheets

U.S. PATENT DOCUMENTS

| | | | |
|---|---|---|---|
| 6,221,024 B1 | 4/2001 | Miesel | 600/486 |
| 6,466,819 B1* | 10/2002 | Weiss | 607/5 |
| 6,487,442 B1 | 11/2002 | Wood | 600/515 |
| 6,675,043 B1* | 1/2004 | Prutchi et al. | 607/17 |
| 2002/0120306 A1* | 8/2002 | Zhu et al. | 607/25 |
| 2003/0181951 A1 | 9/2003 | Cates | 607/9 |
| 2003/0191403 A1 | 10/2003 | Zhou et al. | 600/515 |
| 2004/0044374 A1* | 3/2004 | Weinberg et al. | 607/25 |
| 2005/0043652 A1* | 2/2005 | Lovett et al. | 600/595 |

FOREIGN PATENT DOCUMENTS

| | | |
|---|---|---|
| EP | 1 023 918 A2 | 8/2000 |

OTHER PUBLICATIONS

Exner, D.V. et al., "Electrical Storm Presages Nonsudden Death: The Antiarrhythmics Versus Implantable Defibrillators (AVID) Trial," *Circulation*, vol. 103, p. 2066-2071 (Apr. 24, 2001).

Groenefeld et al., *European Heart Journal*, vol. 21 (supp), p. 199 (2000).

Porterfield, J.G. et al., "Daily Variations in the Occurrence of Symptomatic Supraventricular Tachycardia as Determined by Ambulatory Event Monitoring," *Am J Cardiol.*, vol. 80, No. 7, p. 889-91 (Oct. 1, 1997).

Schmidt, G. et al., "Heart-Rate Turbulence After Ventricular Premature Beats as a Predictor of Mortality After Acute Myocardial Infarction," *Lancet*, vol. 353, p. 1390-96 (Apr. 24, 1999).

Shusterman, V. et al., "Autonomic Nervous System Activity and the Spontaneous Initiation of Ventricular Tachycardia," *J Am Coll Cardiol.*, vol. 32, No. 7, p. 1891-9 (Dec. 1998).

Zhou, X. et al., "Changes in R-R Intervals During Ventricular Tachyarrhythmia Storms in Patients with Implantable Cardioverter-Defibrillator," *J Am Coll Cardiol.*, vol. 39 (suppl. A), p. 86A-87A (Mar. 6, 2002).

* cited by examiner

METHOD AND APPARATUS FOR PREDICTING ARRHYTHMIAS USING DIURNAL HEART RATE

RELATED APPLICATION

The present invention claims priority and other benefits from U.S. Provisional Patent Application Ser. No. 60/526,563, filed Dec. 3, 2003, entitled "METHOD AND APPARATUS FOR PREDICTING ARRHYTHMIAS USING DIURNAL HEART RATE", incorporated herein by reference in its entirety.

FIELD OF THE INVENTION

The present invention relates to implantable medical devices and, more particularly, to a method and apparatus for predicting arrhythmias to enable deployment of targeted interventions for prevention prior to the occurrence of the predicted arrhthmia.

BACKGROUND OF THE INVENTION

Implantable medical devices, referred to as implantable cardioverter defibrillators or ICDs, are capable of automatically detecting arrhythmias, such as ventricular tachycardia (VT) and ventricular fibrillation (VF), and delivering anti-arrhythmia therapies. Delivering anti-tachycardia pacing therapies or high-energy shock therapies may terminate VT and VF. Ventricular tachycardia termination is typically referred to as "cardioversion." Ventricular fibrillation termination is typically referred to as "defibrillation."

Nearly all of detected arrhythmias appropriately treated by an ICD do not result in death. However, some patients with ICDs do experience fatal arrhythmias. Compromised hemodynamic output during a VT or VF episode can render a patient unconscious resulting in related serious injuries or death. Patients may experience recurrent VT or VF and be subjected to repeated shock therapies, which cause great discomfort. Because of the serious consequences, it is desirable to predict the occurrence of VT and VF so that an ICD can be prepared to immediately deliver a therapy or take preventive measures to prevent the occurrence. Prediction of an imminent VT or VF episode also enables preventive medical treatments to be delivered.

A number of parameters for predicting a discreet VT or VF episode have been proposed including, for example, left ventricular dysfunction, myocardial ischemia, frequency of ventricular ectopic beats, heart rate variability, heart rate turbulence, or other electrocardiographic changes (see Shusterman et al., J Am Coil Cardiol. 1998;32:1891-9, and Schmidt et al., Lancet. 1999;353:1390-96). Changes in the autonomic nervous system are known contributing factors to arrhythmogenesis. The heart rate is normally regulated by a balance between the sympathetic and parasympathetic (vagal) components of the autonomic nervous system. Increased sympathetic activity, referred to as sympathetic tone, increases the heart rate and decreases heart rate variability. Increased vagal tone decreases the heart rate and increases heart rate variability. Heart rate variability (HRV) is the variation in consecutive heart rate cycles, which may be measured as ventricular cycle intervals, known as "R-R intervals," or as atrial cycle intervals, known as "A-A intervals." Changes in autonomic tone, especially in conjunction with myocardial ischemia, however, can play an important role in the development of arrhythmias. Therefore, indicators of changes in autonomic tone may be useful in predicting arrhythmias. Reference is made to U.S. Pat. No. 5,042,497 issued to Shapland.

Some patients experience recurring VT or VF episodes. Based on the ICD database, a majority of VTNF episodes occur in forms of "electrical storms" or "clustering" that is defined as a rate of 3 or more VTNF episodes within a 24-hour period (see Groenefeld et al., European Heart Journal. 2000;21(suppl):199, and Zhou et al., J. Am. Coll. Cardiol. 2002;39(suppl. A):86A-87A). Patients who experience electrical storms are at greater risk for subsequent death than patients who experience discreet episodes of VT or VF. Electrical storms are estimated to occur in approximately 10 to 30% of patients having ICDs. (See Bansch et al., J. Am. Coll. Cardiol., 2000;36:566-73, and Exner et al., Circulation., 2001; 103:2066-2071.)

BRIEF DESCRIPTION OF THE DRAWINGS

Aspects and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE INVENTION

As described above, the present invention is directed to predicting arrhythmia, such as ventricular tachycardia, for example, using a quantitative measure in order to allow assessment of patient risk and to enable preventative interventions by the device and clinicians. The trending of day and night average heart rates, along with patient physical activity can be analyzed to provide prediction of impending arrhythmia within weeks. By examining day and night average heart rate for crossover points, where the night heart rate equals or exceeds the day rate, and monitoring for a concomitant elevation in the night heart rate from a reference value, specific days heralding an increased risk of arrhythmia can be determined.

The methods included in the present invention may be incorporated in an implantable or external monitoring device, or an implantable or external cardiac rhythm management device. In a preferred embodiment, the methods of the present invention are incorporated in an implantable cardiac device capable of monitoring the heart rhythm for detecting arrhythmias and delivering anti-arrhythmia therapies, such as the implantable cardioverter defibrillator (ICD) 10 shown in FIG. 1.

Figure 1:
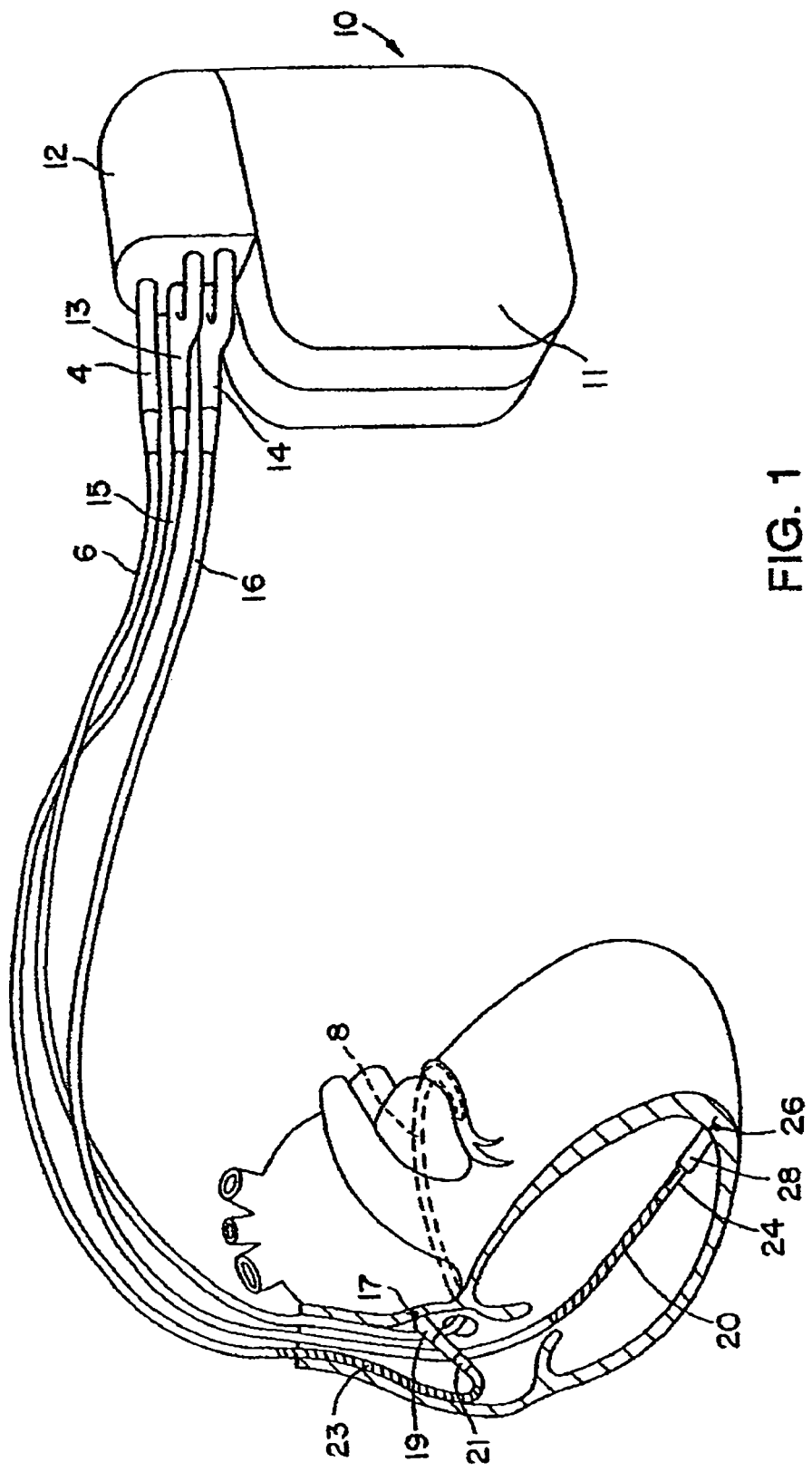
FIG. 1 is an illustration of an implantable cardiac stimulation device capable of pacemaking, cardioversion, and defibrillation and in communication with a patient's heart via three stimulation and sensing leads.

ICD 10 is shown coupled to a patient's heart by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 1, the right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the ICD 10.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the coil electrodes 8, 20 or 23 for defibrillation of the atria or ventricles. It is recognized that alternate lead systems may be substituted for the three lead system illustrated in FIG. 1.

Although three or four-chamber pacing, cardioversion and defibrillation capacity is not necessary for practicing the invention, and indeed detection of ventricular tachycardia or fibrillation can be determined by sensing only signals derived from the right ventricle, a multi-chamber system is illustrated so as to indicate the scope of the invention. It is understood that the invention may normally be practiced with a multi-chamber, dual chamber, or single chamber device.

Figure 2:
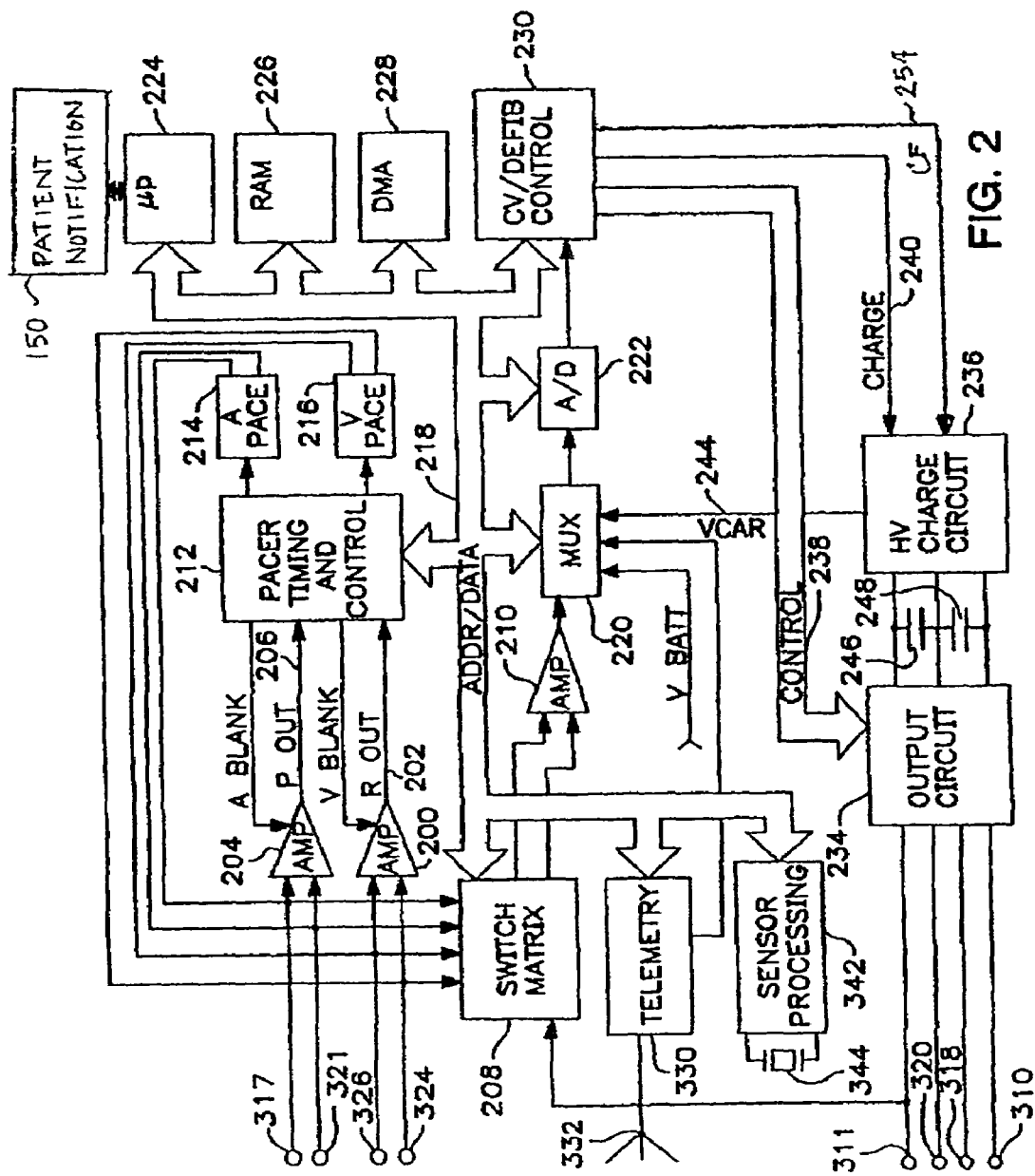
FIG. 2 is a functional, block diagram of the implantable cardiac stimulation device shown in FIG. 1.

A functional schematic diagram of the ICD 10 is shown in FIG. 2. This diagram should be taken as exemplary of the type of device in which the invention may be embodied and not as limiting. The disclosed embodiment shown in FIG. 2 is a microprocessor-controlled device, but the methods of the present invention may also be practiced in other types of devices such as those employing dedicated digital circuitry.

With regard to the electrode system illustrated in FIG. 1, the ICD 10 is provided with a number of connection terminals for achieving electrical connection to the leads 6, 15, and 16 and their respective electrodes. The connection terminal 311 provides electrical connection to the housing 11 for use as the indifferent electrode during unipolar stimulation or sensing. The connection terminals 320, 310, and 318 provide electrical connection to coil electrodes 20, 8 and 28 respectively. Each of these connection terminals 311, 320, 310, and 318 are coupled to the high voltage output circuit 234 to facilitate the delivery of high energy shocking pulses to the heart using one or more of the coil electrodes 8, 20, and 28 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10.

Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known in the art. A tachyarrhythmia recognition mechanism is described in the previously referenced U.S. Pat. No. 5,545,186 issued to Olson et al, incorporated herein by reference in its entirety.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. Received telemetry is provided to microprocessor 224 via multiplexer 220. Numerous types of telemetry systems known for use in implantable devices may be used. The telemetry circuit 330 is also used for communication with a patient activator in one embodiment of the present invention.

In a preferred embodiment, the device 10 is equipped with a sensor 344 and sensor processing circuitry 342. Depending on the type of sensor used, the sensor 344 may be located within the device housing 10 or external to the device housing 10 but implanted within the body of the patient. In one embodiment, the sensor 344 is used for determining the patient's activity level. The sensor 344 may take the form of a piezoelectric crystal as generally described in U.S. Pat. No. 4,428,378 issued to Anderson et al., incorporated herein by reference in its entirety.

The sensor 344 may also represent a pressure sensor for sensing a patient's blood pressure within the heart chambers or vasculature. A change in blood pressure can trigger an autonomic response, and therefore, in one embodiment of the present invention, monitoring a patient's blood pressure may be advantageous in assessing autonomic tone and predicting an electrical storm. Pressure sensors that may be implemented with the ICD 10 are generally described in U.S. Pat. No. 6,171,252 to Roberts, and U.S. Pat. No. 6,221,024 to Miesel, both patents incorporated herein by reference in their entirety.

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

The microprocessor 224 includes associated ROM in which stored programs controlling the operation of the microprocessor 224 reside. A portion of the memory 226 may be configured as a number of re-circulating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microcontroller 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, the ICD 10 may be equipped with a patient notification system 150 used to notify the patient that a recurring VT or VF episode is predicted. Any known patient notification method may be used such as generating a perceivable twitch stimulation or an audible sound under the control of microprocessor 224. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al., incorporated herein by reference in its entirety.

Figure 3:
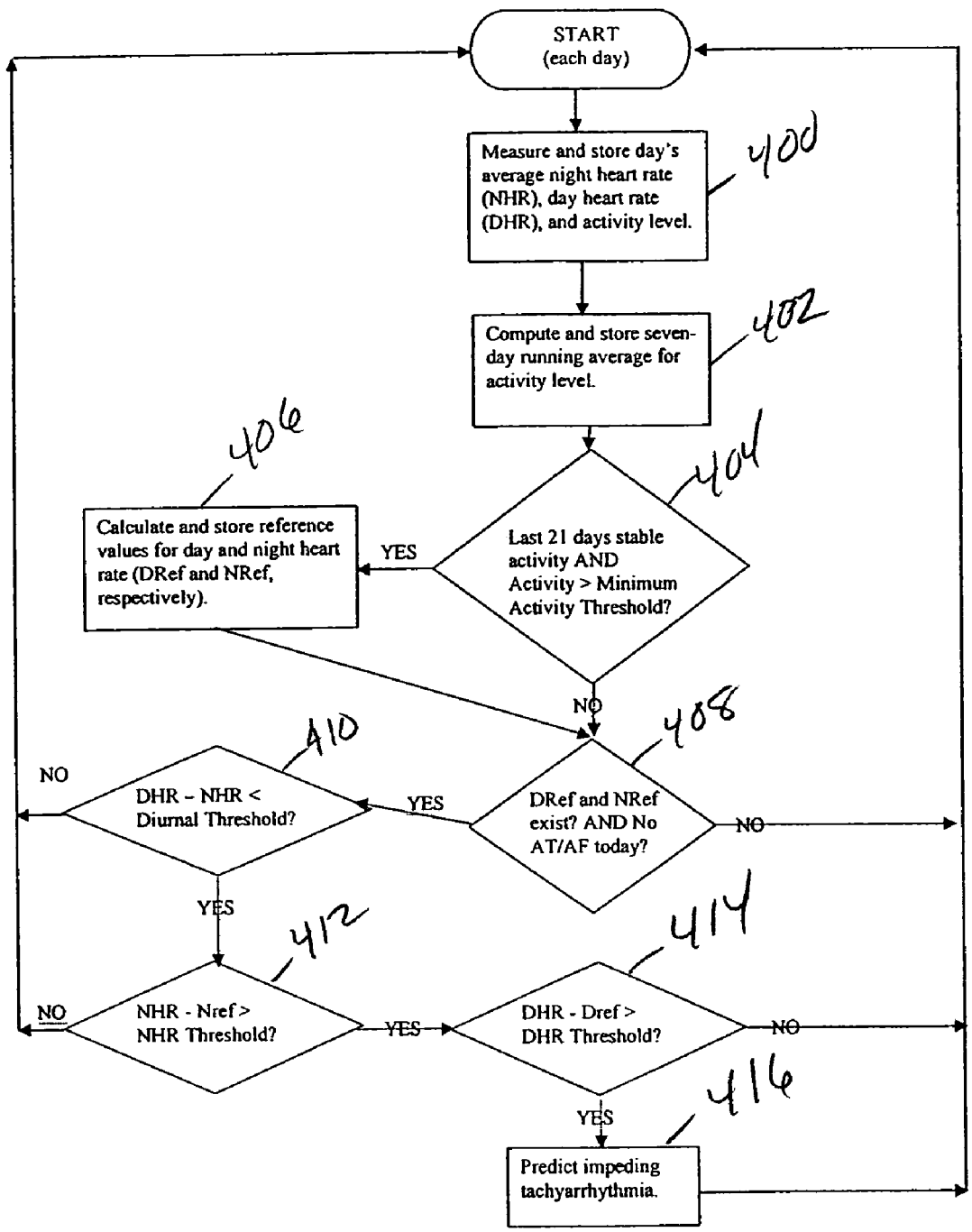
FIG. 3 is a flow chart illustrating a method performed by a medical device for example, for predicting an arrhythmia according to the present invention.

FIG. 3 is a flow chart illustrating a method performed by a medical device for predicting an arrhythmia according to the present invention. As illustrated in FIG. 3, the present invention is embodied in a medical device that monitors the heart rate of the patient on serial days, along with the physical activity of the patient via a means that produces relative measures of activity as known in the art, such as an accelerometer, for example. The day is divided up into a night period and a day period, the rates for each period are determined by averaging all the cardiac intervals occurring during the period. The night period is chosen to reflect the most likely time for the patient to be asleep (here specifically midnight to 04:00). The day period is meant to cover the range of time in which the patient is expected to engage in physical activity (here 08:00 to 20:00). If atrial fibrillation or flutter occurs during the day, it is not used and no prediction attempt is made for the day and the day is not used as a reference toward future days. Each day, the day heart rate and the night heart rate are compared to each other. If the night heart rate meets or exceeds the day heart rate, and the day and night heart rate exceed reference values based on the patient history of rates, then the day's information is considered a prediction of tachyarrhythmic activity within the next day to two weeks.

The determination of the reference values for day and night heart rate is related to patient activity. The most recent three week period for which the maximum 7-day averaged activity measure is no more than 20% greater than the minimum 7-day averaged activity measure is used to compute the references. The day heart rate reference is the average of the average day heart rates in the period. The night heart rate reference is the average of the night heart rates in the period. The heart rate references should be no older than 12 months from the current day, and may occur more often. An absolute lower bound on the number of averages in the reference period and a lower bound on the average activity levels may also be applied in determining a valid reference period.

In particular, as illustrated in FIG. 3, an average night heart rate NHR) and an average day heart rate (DHR), along with an activity level are calculated each day, Block 400. Once a running average for activity level is determined over a predetermined period of time, Block 402, such as seven days for example, a determination is made both as to whether the patient has experienced stable cardiac activity over a predetermined period of time, such as 21 days, for example, and whether the running average for activity level is greater than a predetermined minimum activity threshold, Block 404.

If the patient has experienced stable cardiac activity and the running average for activity level exceeds the threshold, YES in Block 404, a reference value for the day heart rate Dref and a reference value for the night heart rate Nref are calculated and stored, Block 406. Once the reference values for the day and night heart rate are calculated and stored, or if it is determined that the patient has not experienced stable cardiac activity and the running average for activity level exceeds the threshold, NO in Block 404, a determination is made as to whether the night heart rate reference Nref and day heart rate reference Dref have been calculated and the patient has experienced stable cardiac activity for the current day, Block 408. If the night heart rate reference Nref and day heart rate reference Dref have not been calculated or the patient has not experienced stable cardiac activity for the current day, the process waits for the rate and activity levels for the next day. If both the night heart rate reference Nref and day heart rate reference Dref have been calculated and the patient has experienced stable cardiac activity for the current day, a determination is made as to whether the difference between the average day heart rate and the average night heart rate is less than a diurnal threshold, Block 410.

If the difference between the average day heart rate and the average night heart rate is greater than or equal to the diurnal threshold, NO in Block 410, the process waits for the rate and activity levels for the next day. If the difference between the average day heart rate and the average night heart rate is less than the diurnal threshold, YES in Block 410, a determination is made as to whether the difference between the average night heart rate and the reference value for the night heart rate is greater than a night heart rate threshold, Block 412. If the difference between the average night heart rate and the reference value for the night heart rate is less than or equal to the night heart rate threshold, NO in Block 412, the process waits for the rate and activity levels for the next day. If the difference between the average night heart rate and the reference value for the night heart rate is greater than the night heart rate threshold, YES in Block 412, a determination is made as to whether the difference between the average day heart rate and the reference value for the day heart rate is greater than a day heart rate threshold, Block 414. If the difference between the average day heart rate and the reference value for the day heart rate is not greater than the day heart rate threshold, NO in Block 414, the process waits for the rate and activity levels for the next day. If the difference between the average day heart rate and the reference value for the day heart rate is greater than the day heart rate threshold, YES in Block 414, an impending tachyarrhythmias is predicted and preventative measures are taken, Block 416.

In this way, the present invention provides a method and apparatus for signaling increased risk to patient and clinician, and using prediction to instigate preventative therapeutic actions such as pacing, drug interventions, spinal cord stimulation, and others actions known in the art.

Thus, a method and apparatus have been described for predicting a recurring arrhythmia. While the methods included in the present invention have been described in relation to recurring VT or VF episodes, the methods described herein could readily be applied in predicting other arrhythmias, such as recurring atrial arrhythmias. Furthermore, aspects included in the present invention described in conjunction with an ICD could also be implemented in external cardioverter defibrillators, external or internal cardiac rhythm monitoring devices, or external or internal rhythm management devices, which may include drug pumps or neurostimulators. As such, the above disclosure should be considered exemplary, rather than limiting, with regard to the following claims.

We claim:

1. A method of automatically predicting the occurrence of arrhythmias in a patient for use in a medical device, comprising:
    monitoring a heart rate;
    determining the heart rate corresponding to a plurality of predetermined time periods, wherein the plurality of predetermined time periods include a first time period corresponding to the patient being asleep and a second time period corresponding to physical activity of the patient;
    predicting an arrhythmia event in response to the determined heart rates;
    delivering a preventative therapy in response to the predicted arrhythmia event;
    monitoring physical activity of the patient;
    comparing the determined heart rate corresponding to the first time period and the determined heart rate according to the second time period; and
    determining whether the determined heart rate corresponding to the first time period is greater than a first threshold and whether the determined heart rate according to the second time period is greater than a second threshold, wherein predicting an arrhythmia event includes predicting an arrhythmia event in response to the determined heart rate corresponding to the first time period being greater than the determined heart rate according to the second time period, and the determined heart rate corresponding to the first time period being greater than the first threshold and the determined heart rate according to the second time period being greater than the second threshold.

2. The method of claim 1, wherein the first threshold and the second threshold correspond to the monitored physical activity of the patient.

3. The method of claim 1, wherein the preventative therapy includes generating a notification of the predicted arrhythmia.

4. A method of automatically predicting the occurrence of arrhythmias in a patient for use in a medical device, comprising:
    determining a first average rate corresponding to a first portion of a day and a second average rate corresponding to a second portion of the day;
    determining an average activity level over a predetermined period of time;
    calculating a first reference value associated with the first average rate and a second reference value associated with the second average rate;
    determining whether the difference between the first average rate and the second average rate is less than a diurnal threshold;
    determining whether the difference between the second average rate and the second reference value is greater than a second average rate threshold; and
    determining whether the difference between the first average rate and the first reference value is greater than a first average rate threshold;
    predicting an arrhythmia event in response to one of the difference between the first average rate and the second average rate being less than the diurnal threshold, the difference between the second average rate and the second reference value being greater than the second average rate threshold, and the difference between the first average rate and the first reference value being greater than the first average rate threshold; and
    delivering a preventative therapy in response to the predicted arrhythmia event.

* * * * *